(12) United States Patent
Hitzfeld et al.

(10) Patent No.: US 9,332,777 B2
(45) Date of Patent: May 10, 2016

(54) CAROTENOID COMPOSITIONS CONTAINING MODIFIED GUM ACACIA

(75) Inventors: Andrea Hitzfeld, Rheinfelden (DE); Bruno H. Leuenberger, Rheinfelden (CH); Olivia Vidoni, Saint Louis (FR)

(73) Assignee: DSM IP ASSETS B.V., TE Heerlen (NL)

( * ) Notice: Subject to any disclaimer, the term of this patent is extended or adjusted under 35 U.S.C. 154(b) by 274 days.

(21) Appl. No.: 13/326,352

(22) Filed: Dec. 15, 2011

(65) Prior Publication Data
US 2012/0149782 A1 Jun. 14, 2012

Related U.S. Application Data (63) Continuation of application No. 12/529,048, filed as application No. PCT/EP2008/000240 on Jan. 15, 2008, now abandoned.

(30) Foreign Application Priority Data

Mar. 15, 2007 (EP) ..................................... 07005410

(51) Int. Cl.
| | | |
|---|---|---|
| *A61K 36/48* | (2006.01) | |
| *A23L 1/275* | (2006.01) | |
| *A23D 7/005* | (2006.01) | |
| *A23K 1/16* | (2006.01) | |
| *A23L 1/053* | (2006.01) | |
| *A23L 2/52* | (2006.01) | |
| *A23L 2/58* | (2006.01) | |
| *A61K 8/73* | (2006.01) | |
| *A61K 8/97* | (2006.01) | |
| *A61Q 19/10* | (2006.01) | |
| *C08B 37/00* | (2006.01) | |
| *C08K 5/00* | (2006.01) | |
| *C08K 5/01* | (2006.01) | |
| *C08L 5/00* | (2006.01) | |
| *A61Q 1/06* | (2006.01) | |
| *A61Q 5/02* | (2006.01) | |
| *A61Q 5/12* | (2006.01) | |
| *A61Q 19/00* | (2006.01) | |

(52) U.S. Cl.
CPC ............. *A23L 1/2753* (2013.01); *A23D 7/0053* (2013.01); *A23K 1/164* (2013.01); *A23K 1/1606* (2013.01); *A23K 1/1643* (2013.01); *A23L 1/053* (2013.01); *A23L 2/52* (2013.01); *A23L 2/58* (2013.01); *A61K 8/732* (2013.01); *A61K 8/97* (2013.01); *A61Q 19/10* (2013.01); *C08B 37/0087* (2013.01); *C08K 5/005* (2013.01); *C08K 5/01* (2013.01); *C08L 5/00* (2013.01); *A23V 2002/00* (2013.01); *A61K 2800/42* (2013.01); *A61Q 1/06* (2013.01); *A61Q 5/02* (2013.01); *A61Q 5/12* (2013.01); *A61Q 19/00* (2013.01)

(58) Field of Classification Search
CPC ... A61K 9/205; A61K 9/0014; A61K 9/0056; A61K 36/42; A61K 8/97; A61K 36/534
USPC .......................................... 424/485, 493, 758
See application file for complete search history.

(56) References Cited

U.S. PATENT DOCUMENTS

| | | | |
|---|---|---|---|
| 2001/0009679 A1 | 7/2001 | Chen | |
| 2010/0028466 A1 | 2/2010 | Hitzfeld | |

FOREIGN PATENT DOCUMENTS

| | | | |
|---|---|---|---|
| EP | 1 505 078 | | 2/2005 |
| EP | 1505078 A1 | * | 2/2005 |
| EP | 1 772 483 | | 4/2007 |
| JP | 2000-166489 | | 6/2000 |
| WO | 01/09679 | | 2/2001 |
| WO | 2004/089991 | | 10/2004 |
| WO | WO 2004089991 A1 | * | 10/2004 |
| WO | 2006/053761 | | 5/2006 |
| WO | WO 2006053761 A2 | * | 5/2006 |
| WO | 2007/009601 | | 1/2007 |

OTHER PUBLICATIONS

Lakkis. Encapsulation and Controlled Release Technologies in Food Systems. John Wiley and Sons. 2007. p. 51.*
Nussinovitch. Hydrocolloid Applications: Gum Technology in the Food and Other Industries. Springer 1997. p. 248.*
Frost & Sullivan. Beta-Carotene: The Colour of Life. Feb. 21, 2005. Retrieved from the internet. <http://www.frost.com/prod/servlet/market-insight-top.pag?docid=32378173?..Retrieved on Jun. 14, 2011.2 Pages.*
International Search Report for PCT/EP2008/000240, mailed Mar. 28, 2008.
Lakkis, Encapsulation and Controlled Release Technologies in Food Systems. John Wiley & Sons, 2007, p. 51.
Nussinovitch, Hydrocolloid Applications: Gum Technology in the Food and Other Industries. Springer 1997, p. 248.
Frost & Sullivan, Beta-Carotene: The Colour of Life, Feb. 21, 2005. Retrieved from the internet. <http://www.frost.com/prod/servlet/market-insight-top.pag?docid-32378173?.. Retrieved on Jun. 14, 2011. 2 pages.

* cited by examiner

*Primary Examiner* — Chris R Tate
*Assistant Examiner* — Deborah Davis
(74) *Attorney, Agent, or Firm* — Nixon & Vanderhye P.C.

(57) ABSTRACT

Compositions containing modified gum acacia, less than 40% oil and carotenoids, where the gum acacia has been subjected to a heat-treatment at a temperature between 100° C. and 115° C. for 1 to 38 hours. These compositions allow preparation of emulsions having a very high color intensity and color stability and useful for the enrichment, fortification and/or coloration of food beverages, animal feed, cosmetics or pharmaceutical compositions.

11 Claims, 4 Drawing Sheets

CAROTENOID COMPOSITIONS CONTAINING MODIFIED GUM ACACIA

This application is a continuation of application Ser. No. 12/529,048 filed Aug. 28, 2009, which in turn is the U.S. national phase of International Application No. PCT/EP2008/000240, filed 15 Jan. 2008, which designated the U.S. and claims priority to Europe Application No. 07005410.1, filed 15 Mar. 2007, the entire contents of each of which are hereby incorporated by reference.

The present invention relates to compositions containing gum acacia and carotenoids, wherein the gum acacia has been subjected to a heat-treatment at a temperature between 100° C. and 115° C. for 1 to 38 hours, wherein the composition comprises less than 40 weight-% oil, based on the total composition in dry matter. These compositions can be used for the enrichment, fortification and/or coloration of food beverages, animal feed, cosmetics or pharmaceutical compositions. The present invention also refers to the preparation of such compositions. The present invention also refers to modified gum acacia, obtainable by subjecting gum acacia to a heat-treatment at a temperature between 65° C. and 90° C. for 1 to 38 hours. The present invention furthermore refers to a process for the manufacture of a beverage by mixing the compositions with ingredients of beverages. The present invention also refers to beverages obtainable by this process. The present invention furthermore relates to modified gum acacia, obtainable by ultrafiltration of an aqueous solution of gum acacia.

Compositions to enrich, fortify or colorate food, beverages, animal feed, cosmetics or pharmaceutical compositions which contain carotenoids, for example β-carotene, are known in the art. β-Carotene is a preferable colorant compound due to its intense and for the above-mentioned applications very pleasing orange color. Since β-carotene is fat-soluble and the final compositions are usually aqueous compositions such as beverages, additional compounds have to be added to compositions for the enrichment, fortification and/or coloration to avoid separation of β-carotene-containing phases from the product, which separation would render the corresponding product unacceptable.

Therefore, carotenoids are often combined with auxiliary compounds such as starches or fish gelatin, in order to prevent phase separation in a carotenoid containing aqueous composition. Those auxiliary compounds, however, often have an negative influence on the color properties and the nutritional properties of the final products. It is therefore desired to develop new carotenoid compositions, which have a high color intensity. Especially, there is need for improved auxiliary compounds, which have very good properties referring to taste, emulsification, emulsion stability, film forming ability and color of the composition.

Gum acacia (also called gum arabic), a natural hydrocolloid is widely used as an emulsifier/stabilizer in beverage emulsions. It is highly water soluble (up to 50% in weight) and its aqueous solution provides emulsifiability, emulsion stability, encapsulation and film forming ability. Gum acacia is obtained as sticky exudates from the stems and branches of acacia trees when they are subjected to stress. The gum is collected from *Acacia senegal* trees and, to a lesser extent, from *Acacia seyal* trees in several countries in the Sahara region of Africa. It is an arabinogalactan polysaccharide with rhamnose and glucoronic acid end units containing two percent proteins (OH-proline, serine, proline) and four sugars (L-arabinose, L-rhamnose, D-galactose, D-glucuronicacid) (Idris et al, Food Hydrocolloids, Part I to III, 12, 1998, 379-388).

*Acacia senegal* (*A. senegal*) is the most common commercial gum arabic, and also the most available gum. The other gum available, *Acacia seyal* (*A. seyal*), has lower emulsifying properties than *Acacia senegal* but is cheaper. However, gum acacia is considered not as good emulsifier as gelatin, emulsifier commonly used in products, and is not standardized. Uneven performances of the gum may arise among different shipment because of dissimilar functionality related to species, geographical location, and individual growing season. Moreover, the performance of gum arabic depends on the soil, climate, and age of the trees.

WO 2004/089991 discloses a heat-treatment of gum acacia for at least 10 hours at 110° C. but preferably more than 48 hours. However, not all carotenoid compositions heated for a 10 to 72 hours (according to WO 2004/089991) have a high color intensity and color stability. It has unexpectedly been found that the modified gum acacia does confer superior properties to the carotenoid composition, when subjected to a heat treatment according to the present invention. It has also been unexpectedly found that e.g. the color properties of the carotenoid compositions can be further improved when using less amounts of oil as disclosed in WO 2004/089991.

In addition to be used as emulsifier, gum acacia is one of the most common carrier materials with carbohydrates such as hydrolyzed starches. In flavor industry, gum arabic is used as fixative in spray dried application where the gum encapsulates the flavor compound, protecting it against oxidation and volatilization. Few works have shown that blends of gum acacia (Krishnan et al., Carbohydrates Polymers, 61, 2005, 95-102; Krishnan et al. Carbohydrates Polymers, 62, 2005, 309-315; Buffo et al, Perfumers & Flavorist, 25, 2000, 45-54), maltodextrin and modified food starches may represent an encapsulating matrix with improved properties regarding flavor retention and protection against oxidation.

In coloring products, such as beverages, it is also often desirable to preserve the optical clarity of the beverage. Fat-soluble colorants, such as carotenoids, e.g. β-carotene, for supplementation are available in many forms, but when added to beverages, will tend to increase the visible turbidity. Ringing, i.e. the formation of a separate fat-soluble β-carotene layer on the top of the liquid, is also a problem of many known β-carotene formulations. One means of adding fat-soluble substances to beverages without increasing visible turbidity or ringing is to encapsulate the substances in liposomes. However, this is a costly process, and the concentration of substance in the liposome tends to be low.

A satisfactory composition of a fat-soluble colorant, such as a carotenoids, which can be added to beverages in a restorative or nutritionally supplemental amount should thus not affect the optical clarity of the beverage and not alter the sensory properties of the beverage to which it is added. The powder composition should not cause ringing.

Therefore, there is still a need for carotenoid compositions for the enrichment, fortification and/or coloration of food, beverages, animal feed, cosmetics or pharmaceutical compositions which do not show the above-mentioned problems, i.e. which do not show separation phenomena and which provide an increased color intensity and color stability of the resulting product.

It was therefore an object of the present invention to provide carotenoid compositions having an improved color intensity and color stability. These compositions should additionally have the desired properties as indicated above, e.g. very good properties referring to optical clarity and emulsion stability. A further object was to develop improved auxiliary compounds or combinations of such compounds which have high emulsification properties and which can be used to provide such compositions. It was also an object of the invention to improve the process for the preparation of carotenoid compositions for example by reducing the emulsification time of the process.

This objective has been solved by the compositions according to the present invention, which comprise carotenoids and modified gum acacia, wherein the compositions contain less than 40 weight-% oil, based on the total composition in dry matter. Furthermore, the emulsifying performances and the intrinsic properties of gum arabic have been specifically modified by means of physical modification (heat-treatment).

The present invention therefore relates to a composition comprising gum acacia and at least one carotenoid, wherein the gum acacia has been subjected to a heat-treatment at a temperature between 100° C. and 115° C., further preferred between 105° C. and 115° C., further preferred between 108° C. and 113° C. and most preferably at about 110° C., for 13 to 38 hours, further preferred for more than 15 and less than 24 hours and further preferred for 16 to 18 hours, wherein the composition comprises less than 40 weight-% oil, further preferred less than 35 weight-% oil, further preferred less than 30 weight-% oil, based on the total composition in dry matter. It is most preferred that no oil is used in the composition.

In an preferred embodiment of the invention, the composition comprises between 0.1 and 50 weight-%, further preferred between 0.1 and 30 weight-%, further preferred between 0.5 and 20 weight-%, further preferred between 0.5 and 15 weight-%, and most preferred between 0.5 and 10 weight-%, carotenoids, based on the total composition in dry matter.

In an even further preferred embodiment of the invention, the composition is characterized in that one of the carotenoids is β-carotene. It is also preferred to use β-carotene as the only carotenoid.

In an further preferred embodiment of the invention, the composition is characterized in that the gum acacia is *Acacia senegal*.

In an further preferred embodiment of the invention, the composition is characterized in that the composition further comprises at least one modified starch. The modified starch of the composition of the present invention is preferably OSA-starch (starch sodium octenyl succinate).

In another preferred embodiment of the invention, the composition is characterized in that the modified starch is Hi-cap 100.

In an even further preferred embodiment of the invention, the composition is characterized in that the composition possesses a color intensity value (E1/1) of at least 1000, wherein the color intensity E1/1 is the absorbance of a 1% solution of the composition and a thickness of 1 cm and is calculated as follows: E1/1=(Amax−A650)*dilution factor/(weight of sample*content of product form in %).

In an further preferred embodiment of the invention, the composition is characterized in that the composition further comprises one or more adjuvants and/or excipients, wherein it is preferred that these adjuvants and/or excipients do not represent an oil.

In an further preferred embodiment of the invention, the composition is characterized in that maltodextrin is used as an adjuvant/excipient.

In another preferred embodiment of the invention, the composition is characterized in that the amount of gum acacia in relation to the total amounts of gum acacia, modified starch and maltodextrin is at least 20 weight-%, further preferred at least 25 weight-%, further preferred at least 30 weight-%, further preferred at least 35 weight-%, further preferred at least 40 weight-%, further preferred at least 45 weight-%, further preferred at least 50 weight-%, further preferred at least 55 weight-%, further preferred at least 60 weight-%, further preferred at least 65 weight-%, further preferred at least 70 weight-%, further preferred at least 75 weight-%, further preferred at least 80 weight-%, and most preferred at least 85 weight-%.

The present invention also refers to modified gum acacia, obtainable by subjecting gum acacia to a heat-treatment at a temperature between 55° C. and 85° C., further preferred 65° C. and 85° C., further preferred 70° C. and 85° C., further preferred 70° C. and 80° C., for 17 to 65 hours, further preferred for 38 to 65 hours, further preferred for 42 to 65 hours, further preferred for 42 to 50 hours.

The invention also relates to a process for the manufacture of a composition as indicated above comprises the following steps (the process can be carried out using the ingredients in amounts as specified herein):

I) dissolving gum acacia, which has been modified by a heat-treatment at a temperature between 100° C. and 115° C. for 1 to 38 hours, in water, II) adding optionally at least one modified starch to the solution of step I), III) adding $CHCl_3$ and the organic phase, comprising at least one carotenoid and less than 40 weight-% oil (based on the total composition in dry matter) and optionally at least one water-soluble excipient and/or adjuvant, to the solution of step II)

IV) emulsifying the mixture of step III) for about 30 minutes at a temperature of between 30° C. and 100° C., further preferred between 45° C. and 80° C., further preferred between 50° C. and 70° C.

evaporating the organic solvent under vacuum.

VI) Drying the emulsion by spray-drying, powder catch or other processes

It is further preferred that polysaccharides, preferably maltodextrin, is added in step II) of the process.

The invention also relates to the use of a composition as indicated above for the enrichment, fortification and/or coloration of food, beverages, animal feed, cosmetics or pharmaceutical compositions.

The invention also relates to a process for the manufacture of a beverage by mixing a composition as indicated above with further usual ingredients of beverages.

The invention also relates to a beverage obtainable by the process as indicated above.

The invention furthermore relates to modified gum acacia, obtainable by ultrafiltration of an aqueous solution of gum acacia.

Preferably, the modified gum acacia is subjected to a heat-treatment as described above before the ultrafiltration step.

It has surprisingly been found that the carotenoid compositions of the present invention comprising a modified gum acacia and less than 30 weight-% oil (based on the total composition in dry matter) and optionally further adjuvants and/or excipients can be mixed with water, whereby the resulting mixture has a high color intensity and color stability. Such a red to orange color is advantageous for the foods, beverages, animal feed, cosmetic or pharmaceutical compositions the composition can be used for. Further, no separation of the carotenoid from the resulting mixture is obtained. The advantageous color is achieved without the presence of auxiliary compounds such as fish gel or coloring compounds beside β-carotene, Up to now, no compositions comprising carotenoids and modified gum acacia and less than 40 weight-% oil (based on the total composition in dry matter), wherein the gum acacia has been modified by a heat-treatment are known. It was therefore surprisingly found that compositions with specifically modified gum acacia and less than 40 weight-% oil (based on the total composition in dry matter) have improved color intensities and high emulsification properties. The unexpected high color values have been achieved by using gum acacia, which has been modified at the specific temperature and specific duration of the heat-treatment according to the present invention.

It has been found that a short heating time (approximately 1 hour) induces a slight increase of the emulsifying properties, whereas a longer (24 hours and higher) one induces the contrary. Therefore, the compositions using the gum acacia according to the invention provide a very high color intensity and good emulsification properties.

It was furthermore unexpectedly found that the specifically modified gum acacia, when used in mixture with a lower molecular weight emulsifier (food modified starch) even further improved the quality of the resulting emulsions, especially the color value. The use of an additional low molecular weight carbohydrate (preferably maltodextrin) proved to be even more advantageous.

It was furthermore unexpectedly found that the compositions according to the present invention have improved properties, e.g. color intensity and color stability, when using a small amount or no oil.

If not defined to the contrary, the amount (weight-%) of a compound of the composition refers to the weight-% of this compound based on the total composition in dry matter (total amount of all ingredients without any solvents like organic solvents or water). The carotenoid compositions according to the invention are preferably emulsions.

The gum acacia used for the preparation of modified gum acacia for the compositions according to the invention is *Acacia senegal* or *Acacia seyal*, preferably *Acacia senegal*. Modifying the gum acacia means to subject the gum acacia to a heat-treatment.

The heat-treatment is carried out at temperatures between 100° C. and 115° C., further preferred between 105° C. and 115° C., further preferred between 108° C. and 113° C. and most preferably at about 110° C. The duration of the heat-treatment process is between 13 and 38 hours, further preferred between more than 15 and less than 24 hours, further preferred between 16 and 20 hours and most preferred between 16 and 18 hours.

Additionally, the heat-treatment process can be performed with or without stirring the gum acacia. The heat-treatment process can furthermore be carried out in an oven preferably using a stainless steel container, which does not have to be sealed. The process and an quality analysis of the obtained gum acacia can be performed as described in WO 2004/089991.

In another embodiment of the invention, modified gum acacia is obtained by subjecting gum acacia to a heat-treatment at a temperature between 55° C. and 85° C., further preferred 65° C. and 85° C., further preferred 70° C. and 85° C., further preferred 70° C. and 80° C., for 17 to 65 hours, further preferred for 38 to 65 hours, further preferred for 42 to 65 hours, further preferred for 42 to 50 hours. The heat-treatment can be carried out in solid state or in aqueous solution (compare example 10), preferably in aqueous solution. The modified gum acacia, which is obtained at these lower temperatures can also be used for all the compositions as described herein.

In an further embodiment of the invention, the modified gum acacia is obtained by ultrafiltration of an aqueous solution of gum acacia. Additionally, the modified gum acacia is obtained by ultrafiltration of an aqueous solution of gum acacia, which has been subjected to a heat treatment. The heat-treatment can be performed at the different temperatures as described above. Compare examples 3 and 8. The modified gum acacia, obtained by ultrafiltration can be used for all compositions as described herein.

The expression "carotenoid" as used in the context of the invention refers to the group of related substances having the formula $C_{40}H_{56}$. Specific members of this group of carotenoids are: apocarotinal, lutein, asthaxanthin, alpha-carotene (α-carotene), beta-carotene (β-carotene), gamma-carotene (γcarotene), delta-carotene (δ-carotene) and epsilon-carotene (ε-carotene). Beta-carotene (β-carotene) is preferably used in the compositions according to the invention.

Preferably at least one carotenoid of the above indicated group is used, wherein it is preferred that at least beta-carotene (β-carotene) is used. It is also preferred to only use beta-carotene (β-carotene). The amount of carotenoids used in the composition is between 0.1 and 50 weight-%, further preferred between 0.1 and 30 weight-%, further preferred between 0.5 and 20 weight-%, further preferred between 0.5 and 15 weight-%, and most preferred between 0.5 and 10 weight-%.

Additionally, modified starch can be used in the compositions. The modified starch is preferably a modified food starch which is optionally partly hydrolyzed (modified food) starch, crosslinked (modified food) starch, OSA-starch, (modified food) starch, further modified in any physical or chemical way, preferably OSA-starch.

A modified starch is a starch that has been chemically modified by known methods to have a chemical structure which provides it with a hydrophilic and a lipophilic portion. Preferably, a modified starch has a long hydrocarbon chain as part of its structure, preferably a $C_5$-$C_{18}$ alkyl chain, in particular a $C_8$ alkyl chain.

Optionally, one modified starch is preferably used to make a composition of this invention, but it is possible to use a mixture of two or more different modified starches in one composition.

Starches are hydrophilic and therefore do not have emulsifying capacities. However, modified starches are made from starches substituted by non-chemical methods with hydrophobic moieties. For example, the starch may be treated with cyclic dicarboxylic acid anhydrides such as succinic anhydrides, substituted with a hydrocarbon chain (see O. B. Wurzburg (editor), "Modified Starches: Properties and Uses", CRC Press, Inc. Boca Raton, Fla., 1986 (and subsequent editions). A particularly preferred modified starch of this invention has the following formula (I)

wherein St is a starch, R is an alkylene radical and R' is a hydrophobic group. Preferably R is a lower alkylene radical such as dimethylene or trimethylene. R' may be an alkyl or alkenyl group, preferably having 5 to 18 carbon atoms. A preferred compound of formula (I) is an "OSA-starch" (starch sodium octenyl succinate). The degree of substitution, i.e. the number of esterified hydroxyl groups to the number of free non-esterified hydroxyl groups usually varies in a range of from 0.1% to 10%, preferably in a range of from 0.5% to 4%, more preferably in a range of from 3% to 4%.

The term "OSA-starch" denotes any starch (from any natural source such as corn, waxy, maize, waxy corn, wheat, tapioca and potato or synthesized) that was treated with octenyl succinic anhydride (OSA). The degree of substitution, i.e. the number of hydroxyl groups esterified with OSA to the number of free non-esterified hydroxyl groups usually varies in a range of from 0.1% to 10%, preferably in a range of from 0.5% to 4%, more preferably in a range of from 3% to 4%. OSA-starches are also known under the expression "modified food starch".

These OSA-starches may contain further hydrocolloids, such as starch, maltodextrin, carbohydrates, gum, corn syrup etc. and optionally any typical emulsifier (as co-emulgator), such as mono- and diglycerides of fatty acids, polyglycerol esters of fatty acids, lecithins, sorbitan monostearate, and plant fiber or sugar.

The term "OSA-starches" encompasses also such starches that are commercially available e.g. from National Starch under the tradenames Hi-Cap 100, Capsul, Capsul HS, Purity Gum 2000, UNI-PURE, HYLON VII; from Roquette Frères; from CereStar under the tradename C*EmCap or from Tate & Lyle. These commercially available starches are also suitable starting materials for the improved OSA-starches of the present invention. Hi-Cap 100 is preferably used.

The terms "modified starches" and "OSA-starches" encompass further also modified starches/OSA-starches that were partly hydrolyzed enzymatically, e.g. by glycosylases (EC 3.2; see http://www.chem.qmul.ac.uk/iubmb/enzyme/EC3.2/) or hydrolases, as well as to modified starches/OSA-starches that were partly hydrolyzed chemically by know methods. The terms "modified starches" and "OSA-starches" encompass also modified starches/OSA-starches that were first partly hydrolysed enzymatically and afterwards additionally hydrolysed chemically. Alternatively it may also be possible to first hydrolyse starch (either enzymatically or chemically or both) and then to treat this partly hydrolysed starch with cyclic dicarboxylic acid anhydrides such as succinic anhydrides, substituted with a hydrocarbon chain, preferably to treat it with octenyl succinic anhydride.

The enzymatical hydrolysis is conventionally carried out at a temperature of from about 5 to about <100° C., preferably at a temperature of from about 5 to about 70° C., more preferably at a temperature of from about 20 to about 55° C.

The glycosylases/hydrolases can be from fruit, animal origin, bacteria or fungi. The glycolase/hydrolase may have endo-activity and/or oxo-activity. Therefore, enzyme preparations of endo- and exo-glycosylases/-hydrolases or any of their mixtures may be used. Usually the glycosylases/hydrolases show also unknown side activities, but which are not critical for the manufacture of the desired product.

Examples of glycosylases are the commercially available enzyme preparations from the suppliers Novozymes, Genencor, AB-Enzymes, DSM Food Specialities, Amano, etc.

Preferably the hydrolases are α-amylases, glucoamylases, β-amylases or debranching enzymes such as isoamylases and pullulanases.

The glycosylase/hydrolase can be added to the "modified starches" during hydrolysis to provide a concentration of from about 0.01 to about 10 weight-%, preferably of from about 0.1 to about 1 weight-%, based on the dry weight of the modified starch/OSA-starch, preferably the enzyme is added at once. The enzymatic hydrolysis may also be carried out stepwise. For instance, the glycosylase/hydrolase or a mixture of glycosylases/hydrolases is added to the incubation batch in an amount of e.g. 1% whereupon, e.g. after 5 to 10 minutes (at a temperature of 35° C.) further glycosylase/hydrolase or a mixture of glycosylases which may by the same or different from the first added glycosylase/hydrolase or mixture of glycosylases/hydrolases is added, e.g. in an amount of 2% whereupon the incubation batch is hydrolyzed at 35° C. for 10 minutes. Using this procedure, starting modified starches/OSA-starches having a degree of hydrolysis of approximately zero can be used.

The duration of hydrolysis may vary between about a few seconds and about 300 minutes. The exact duration of the enzymatic treatment may be determined in an empirical way with respect to the desired properties of the modified starch/OSA-starch, such as emulsifying stability, emulsifying capacity, droplet size of the emulsion, depending strongly on parameters like enzyme activities, or composition of the substrate. Alternatively it may be determined by measuring the osmolality (W. Dzwokak and S. Ziajka, Journal of food science, 1999, 64 (3) 393-395).

The inactivation of the glycosylase/hydrolase, which is preferably conducted after hydrolysis, is suitably achieved by heat denaturation, e.g. by heating of the incubation batch to about 80 to 85° C. for 5 to 30 minutes, especially for 5 to 10 minutes.

Determination of the color intensity value of the compositions, which correspond to the emulsification properties is performed by measuring the absorbance of the compositions. The color intensity values of the compositions according to the present invention are determined by using a model system containing 4% β-carotene.

To measure the extinction coefficient an adequate amount of the composition is dispersed, dissolved and/or diluted in/with water by use of ultrasonics in a water bath of 50 to 55° C. The resulting "solution" is diluted to a final concentration of the β-carotene of 5 ppm and its UV/VIS-spectrum is measured against water as reference. From the resulting UV/VIS spectrum the absorbance at the specified wavelength of maximum or shoulder. Amax, is determined. Furthermore, the absorbance at 650 nm, A650, is determined. The color intensity E1/1 is the absorbance of a 1% solution and a thickness of 1 cm and is calculated as follows: E1/1=(Amax-A650)*dilution factor/(weight of sample*content of product form in %).

Additionally, the compositions of the present invention may (further) contain one or more excipients and/or adjuvants selected from the group consisting of monosaccharides, disaccharides, oligosaccharides and polysaccharides, water-soluble antioxidants and fat-soluble antioxidants.

Examples of mono- and disaccharides which may be present in the compositions of the present invention are sucrose, invert sugar, xylose, glucose, fructose, lactose, maltose, saccharose and sugar alcohols.

Examples of the oligo- and polysaccharides are starch, starch hydrolysates, e.g. dextrins and maltodextrins, especially those having the range of 5 to 65 dextrose equivalents (DE), and glucose syrup, especially such having the range of 20 to 95 DE. The term "dextrose equivalent" (DE) denotes the degree of hydrolysis and is a measure of the amount of reducing sugar calculated as D-glucose based on dry weight; the scale is based on native starch having a DE close to 0 and glucose having a DE of 100. Preferably, maltodextrin is used in the composition according to the invention.

The expression "oil" as used in this context comprises any triglycerides or any other oil (e.g. terpene), which is suitable for the desired use of the composition. The triglyceride is suitably a vegetable oil or fat, preferably corn oil, sunflower oil, soybean oil, safflower oil, rapeseed oil, peanut oil, palm oil, palm kernel oil, cotton seed oil, orange oil, limonene, olive oil or coconut oil.

The composition according to the invention preferably comprises less than 30%, further preferred less than 28 weight-%, further preferred less than 25 weight-%, further preferred less than 20 weight-%, further preferred less than 18 weight-%, further preferred less than 15 weight-%, further preferred less than 13 weight-%, further preferred less than 10 weight-%, further preferred less than 8 weight-%, further preferred less than 6 weight-%, further preferred less than 3 weight-% oil (based on the total composition in dry matter). Most preferably the composition does not comprise any oil.

Solid compositions may in addition contain an anti-caking agent, such as silicic acid or tricalcium phosphate and the like, and up to 10 weight-%, preferably 0.1 to 5 weight-%.

The water-soluble antioxidant may be for example ascorbic acid or a salt thereof, preferably sodium ascorbate, water-soluble polyphenols such as hydroxy tyrocol and oleuropein, aglycon, epigallo catechin gallate (EGCG) or extracts of rosemary or olives.

The fat-soluble antioxidant may be for example a tocopherol, e.g. dl-α-tocopherol (i.e. synthetic tocopherol), d-α-tocopherol (i.e. natural tocopherol), β- or γ-tocopherol, or a mixture of two or more of these; butylated hydroxytoluene (BHT); butylated hydroxyanisole (BHA); ethoxyquin, propyl gallate; tert. butyl hydroxyquinoline; or 6-ethoxy-1,2-dihydroxy-2,2,4-trimethylquinoline (EMQ), or an ascorbic acid ester of a fatty acid, preferably ascorbyl palmitate or stearate.

Additionally, the composition can comprise water.

Preferably, the compositions of the present invention do not contain further coloring substances except the carotenoid compound. Preferably, the compositions of the present invention do not contain fish gelatin.

Table 2 shows the preferred amounts (weight-%) of ingredients of the composition, based on the total composition in dry matter. The amounts specified in table 2 can additionally be combined with the preferred amounts for the ingredients as specified above.

TABLE 2

| Ingredient | Amount |
| --- | --- |
| Carotenoids, preferably β-carotene | 0.1 to 50 weight-%, preferably 1 to 30 weight-%, preferably 1 to 20 weight-%, preferably 0.5 to 15 weight-%, preferably 0.5 to 10 weight-% |
| gum acacia | 20 to 85 weight-%, preferably 55 to 85 weight-%; |
| modified starch | 0 to 20 weight-%, preferably 10 to 15 weight-% |
| saccharides, preferably maltodextrin | 0 to 20 weight-%, preferably 10 to 15 weight-% |
| a starch hydrolysate | 0 to 20 weight-%, preferably 10 to 15 weight-%; |
| oil | 0 to 40 weight-%, preferably 0 to 10 weight-%; |
| glycerol | 0 to 30 weight-%, preferably 0 to 10 weight-% |
| a triglyceride | 0 to 30 weight-%, preferably 0 to 10 weight-% |
| one or more water-soluble antioxidant(s) | 0 to 5 weight-%, preferably 0 to 2 weight-% |
| one or more fat-soluble antioxidant(s) | 0 to 5 weight-%, preferably 0 to 2 weight-% |
| a starch | 0 to 20 weight-%, preferably 10 to 15 weight-% |
| anti-caking agent | 0.1 to 5 weight-% |

Additionally, the composition can comprise water or any other solvents. If the composition is liquid, it can contain solvents (e.g. water) from few ppm to higher concentration.

In still another aspect of the invention, the compositions according to the invention may additionally contain proteins (of plant or animal origin) or hydrolyzed proteins that act as protective colloids, e.g. proteins from soy, rice (endosperm) or lupine, or hydrolyzed proteins from soy, rice (endosperm) or lupine, as well as plant gums (such as gum acacia or Gum arabic) or modified plant gums. Such additional proteins or plant gums may be present in the formulations of the invention in an amount of from 1 to 50 weight-% based on the total amount of modified starch in the formulation/composition.

Process for the Manufacture of the Compositions According to the Invention

The present invention is further related to a process for the manufacture of such compositions as described above comprising the following steps (the process is also described in the examples). Furthermore, the preferred amounts for the ingredients as specified above can be used for the process.

I) dissolving gum acacia, which has been modified by a heat-treatment at a temperature between 100° C. and 115° C. for 1 to 38 hours, in water.

II) adding optionally at least one modified starch to the solution of step I),

III) adding an organic solvent, as an example CHCl$_3$, and the organic phase, comprising at least one carotenoid and less than 40 weight-% oil (based on the total composition in dry matter) and optionally at least one water-soluble excipient and/or adjuvant, to the solution of step II)

IV) emulsifying the mixture of step III) for about 30 minutes at a temperature of between 30° C. and 100° C.

V) evaporating the organic solvent under vacuum.

VI) Drying the emulsion by spray-drying, powder catch or other processes

Additionally, preferably maltodextrin is added in step II) of the process.

Suitable organic solvents are halogenated aliphatic hydrocarbons, aliphatic ethers, aliphatic and cyclic carbonates, aliphatic esters and cyclic esters (lactones), aliphatic and cyclic ketones, aliphatic alcohols and mixtures thereof.

Examples of halogenated aliphatic hydrocarbons are mono- or polyhalogenated linear, branched or cyclic C$_1$- to C$_{15}$-alkanes. Especially preferred examples are mono- or polychlorinated or -brominated linear, branched or cyclic C$_1$- to C$_{15}$-alkanes. Preferably CHCl$_3$ is used.

Examples of aliphatic esters and cyclic esters (lactones) are ethyl acetate, isopropyl acetate and n-butyl acetate; and γ-butyrolactone.

Examples of aliphatic and cyclic ketones are acetone, diethyl ketone and isobutyl methyl ketone; and cyclopentanone and isophorone.

Examples of cyclic carbonates are especially ethylene carbonate and propylene carbonate and mixtures thereof.

Examples of aliphatic ethers are dialkyl ethers, where the alkyl moiety has 1 to 4 carbon atoms. One preferred example is dimethyl ether.

Examples of aliphatic alcohols are ethanol, iso-propanol, propanol and butanol.

The present invention is also directed to the use of compositions as described above for the enrichment, fortification and/or coloration of food, beverages, animal feed, cosmetics or pharmaceutical compositions, preferably for the enrichment, fortification and/or coloration of beverages. There is no "ringing", i.e. the undesirable separation of insoluble parts at the surface of bottles filled with beverages containing the compositions of the present invention.

Other aspects of the invention are food, beverages, animal feed, cosmetics and pharmaceutical compositions containing a composition as described above.

Beverages wherein the product forms of the present invention can be used as a colorant or an additive ingredient can be carbonated beverages e.g., flavored seltzer waters, soft drinks or mineral drinks, as well as non-carbonated beverages e.g. flavored waters, fruit juices, fruit punches and concentrated forms of these beverages. They may be based on natural fruit or vegetable juices or on artificial flavors. Also included are alcoholic beverages and instant beverage powders. Besides, sugar containing beverages diet beverages with non-caloric and artificial sweeteners are also included.

Further, dairy products, obtained from natural sources or synthetic, are within the scope of the food products wherein the product forms of the present invention can be used as a colorant or as an additive ingredient. Typical examples of such products are milk drinks, ice cream, cheese, yogurt and the like. Milk replacing products such as soymilk drinks and tofu products are also comprised within this range of application.

Also included are sweets which contain the product forms of the present invention as a colorant or as an additive ingredient, such as confectionery products, candies, gums, desserts, e.g. ice cream, jellies, puddings, instant pudding powders and the like.

Also included are cereals, snacks, cookies, pasta, soups and sauces, mayonnaise, salad dressings and the like which contain the product forms of the present invention as a colorant or an additive ingredient. Furthermore, fruit preparations used for dairy and cereals are also included.

The final concentration of the β-carotene which is added via the compositions of the present invention to the food products may preferably be from 0.1 to 50 ppm, particularly from 1 to 30 ppm, more preferred 3 to 20 ppm, e.g. about 6 ppm, based on the total weight of the food composition and depending on the particular food product to be colored or fortified and the intended grade of coloration or fortification.

The food compositions of this invention are preferably obtained by adding to a food product the carotenoid in the form of a composition of this invention. For coloration or fortification of a food or a pharmaceutical product a composition of this invention can be used according to methods per se known for the application of water dispersible solid product forms.

In general the composition may be added either as an aqueous stock solution, a dry powder mix or a pre-blend with other suitable food ingredients according to the specific application. Mixing can be done e.g. using a dry powder blender, a low shear mixer, a high-pressure homogenizer or a high shear mixer depending on the formulation of the final application. As will be readily apparent such technicalities are within the skill of the expert.

Pharmaceutical compositions such as tablets or capsules wherein the compositions of the present invention are used as a colorant are also within the scope of the present invention. The coloration of tablets can be accomplished by adding the compositions in form of a liquid or solid colorant composition separately to the tablet coating mixture or by adding the compositions to one of the components of the tablet coating mixture. Colored hard or soft-shell capsules can be prepared by incorporating the compositions in the aqueous solution of the capsule mass.

Pharmaceutical compositions such as tablets such as chewable tablets, effervescent tablets or film-coated tablets or capsules such as hard shell capsules wherein the compositions of the present invention are used as an active ingredient are also within the scope of the present invention. The product forms are typically added as powders to the tabletting mixture or filled into the capsules in a manner per se known for the production of capsules.

Animal feed products such as premixes of nutritional ingredients, compound feeds, milk replacers, liquid diets or feed preparations wherein the compositions are either used as a colorant for pigmentation e.g. for egg yolks, table poultry, broilers or aquatic animals or as an active ingredient are also within the scope of the present invention.

Cosmetics, toiletries and derma products i.e. skin and hair care products such as creams, lotions, baths, lipsticks, shampoos, conditioners, sprays or gels wherein the compositions of the present invention are used as a colorant or as an additive or as an active ingredient are also within the scope of the present invention.

The beverages and compositions of the present invention are those that show superior behavior in the test methods described below, in particular show an advantageous color hue.

Examples of beverages of the present invention are sports beverages, vitamin supplemented waters and beverages where the addition of vitamins is of interest. Also of interest are beverages used to restore electrolytes lost through diarrhea. Also of interest are carbonated beverages such as flavored seltzer waters, soft drinks or mineral drinks, as well as non-carbonated fruit and vegetable juices, punches and concentrated forms of these beverages.

The present invention further relates to a process for the manufacture of a beverage by mixing an composition as described above with further usual ingredients.

Further, the present invention relates to beverages obtainable by the process for the manufacture of a beverage as described above.

The compositions of the present invention are preferably additive compositions and are preferably used as additive compositions.

The present invention is further illustrated by the following examples, which are not intended to be limiting.

Example 1

Heat-Treatment of the Gum Acacia (*A. senegal* or *A. seyal*)

1 Kg of gum acacia was heated on an oven (SALVIS) at 110° C. during lapse of time from 1 to 72 hours. After 2 hours, gum's color changed to darker and presented a caramel like smelling. After heating process, the gum acacia was placed on a desiccator and used without further modifications.

Example 2

Emulsion Realized with Blend Gum Acacia/Hi-Cap 100/Maltodextrin

On a beaker, 150 g of gum acacia were dissolved into 250 g of water and stirred with IKA-Euro-star at room temperature during one hour. After total dissolution, 31.24 g of Hi-Cap 100 and 31.24 g of maltodextrin were added and the mixture stirred further till complete dissolution. To speed up the dissolving process, the beaker was heated at 35° C. Then, 330 g of this matrix were transferred in a reactor and stirred with a dissolver disc (1000 U/min-Fluid) at 50° C. during 30 min. Meanwhile, the organic phase containing 8.9 g of β-carotene, 9.7 g of corn-oil, 2.7 g of α-tocopherol dissolved in 148 g of chloroform was heated up at 69° C. during 30 minutes under stirring. The emulsification process was broken-up in two parts: first, realization of a premix by addition of 29.6 g of $CHCl_3$ to the aqueous matrix (mixing speed 5400 U/min), and then, addition of the organic phase at the same mixing speed. The resulting product was emulsified during 10 minutes (5000 U/min). Finally, the solvent was evaporated under vacuum (Rotavapor Büchi, Typ R-205) during 1 hour at 45° C.

Example 3

Emulsion Realized with Blend of Heat Treated Gum Acacia/Hi-Cap 100/Maltodextrin

The same procedure as described in example 2 was used. The only difference belongs to the type of gum. Instead of normal gum acacia, gums modified by heat-treatment were used. The modified gums presented no problem of dissolution independently of the heating time. In the case of gum acacia heated for more than 13 hours, increase of the viscosity and a darkening of the resulting matrix were observed.

Example 4

Emulsion Realized with Pure Heat-Treated Gum Acacia

On an ESCO-reactor, 220 g of water were dissolved into 110 g of gum acacia and stirred at room temperature during one hour. To speed up the dissolving process, the reactor was heated at 35° C. Then, the matrix was heated up at 50° C. during 30 min. Meanwhile, the organic phase containing 8.9 g of β-carotene, 9.7 g of corn-oil, 2.7 g of α-tocopherol dissolved in 148 g of chloroform was heated up at 69° C. during 30 minutes under stirring. The emulsification process was broken-up in two parts as above: first, realization of a premix by addition of 29.6 g of $CHCl_3$ to the aqueous matrix (mixing speed 25000 rpm), and then, addition of the organic phase at the same mixing speed. The resulting product was emulsified during 30 minutes (2500 rpm). Finally, the solvent was evaporated under vacuum (Rotavapor Büchi Typ R-205) during 1 hour at 45° C.

Example 5

Ultrafiltration of the Gum Acacia (*A. senegal* or *A. seyal*)

An aqueous solution containing 10% in weight of GA was ultra-filtrated (Cross-flow) through hollow fibers membrane (GE Healthcare) with a molecular weight cut off (MWCO) of 750 kDa. The solution was filtrated at 30° C. with a trans-membrane pressure (TMP) of 1 bar. The process was stopped at a concentration factor (CF) equal to two. The retentate solution was then spray-dried (Niro-Mobile Minor$^{TN}$ "2000"- $T_{in}$: 180° C. $T_{out}$: 80° C.). The collected product was stored and used without any further modifications.

Example 6

Effect of the Blend Gum Acacia/Hi-Cap 100/Maltodextrin

As already mentioned, the parameter selected to evaluate emulsion's quality is the color intensity, E1/1. The carotenoid compositions are classified as follows:

0<E1/1<500: bad emulsion
500<E1/1<1000: acceptable emulsion
E1/1>1000: good emulsion It is desired to provide at least acceptable emulsions, preferably good emulsions with a color intensity value of at least 1000.

Figure 1:
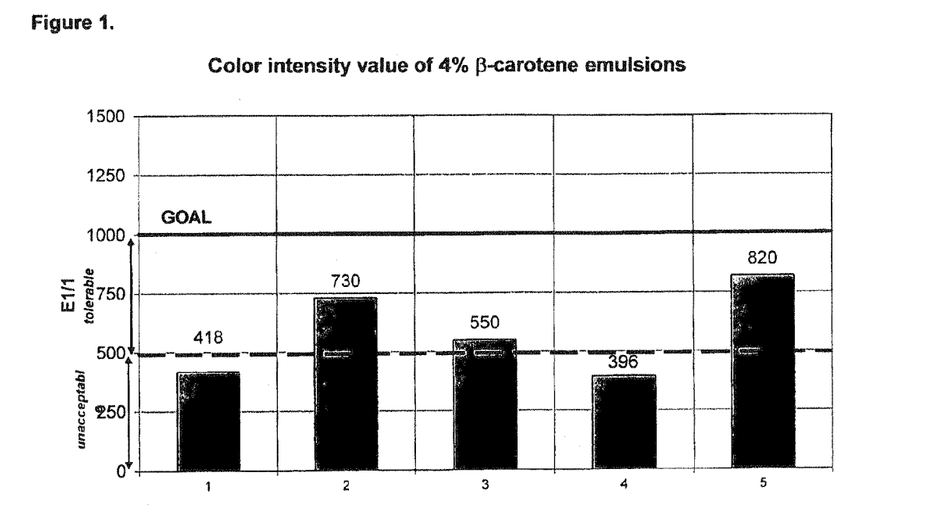
FIG. 1: Influence of the matrix composition and emulsification time (ET) on the colour intensity E1/1 value of several emulsions. The matrix composition is 1) gum acacia (GA). Hi-cap 100, Maltodextrin (MD) according to a ratio 66.6%/16%/16%; ET:30 min, 2) same composition, ET:10 min, 3) GA and Hi-cap 100-ET:10 min; 4) GA and MD-ET:10 min; 5) GA, Hi-cap 100-MD according to a ratio 70.6%/14.6%/14.7%-ET:10 min

Used in a blend with Hi-cap 100 and maltodextrin (MD), emulsification properties of the gum were significantly increased, and its emulsification time (ET) decreased (see FIG. 1).

Emulsions realised with only 2 out of the 3 components mentioned before performed not as good (see FIG. 1). Finally, ratio between each constituent influences the colour intensity (see column 5): a decrease of Hi-cap 100 and MD amounts is converted to a further increase of the E1/1 value.

Example 7

Effect of Heat-Treatment

The modification of gum acacia was performed according to the process as disclosed in WO 2004/089991. WO 2004/089991 describes a significant increase of the emulsifying properties of gum acacia after a heat-treatment at 110° C. not less than 10 hours but preferred conditions reported being between 48 to 72 hours. The theory discloses in WO 2004/089991 is based on an enlargement of the molecular size (not less than 0.9 millions) by maillard reaction to get better emulsifying properties. To verify the applicability of this theory to our specific systems, we heat-treated GA in solid state during different time at 110° C. and used it as emulsifier. Results are presented in FIG. 2.

Figure 2:
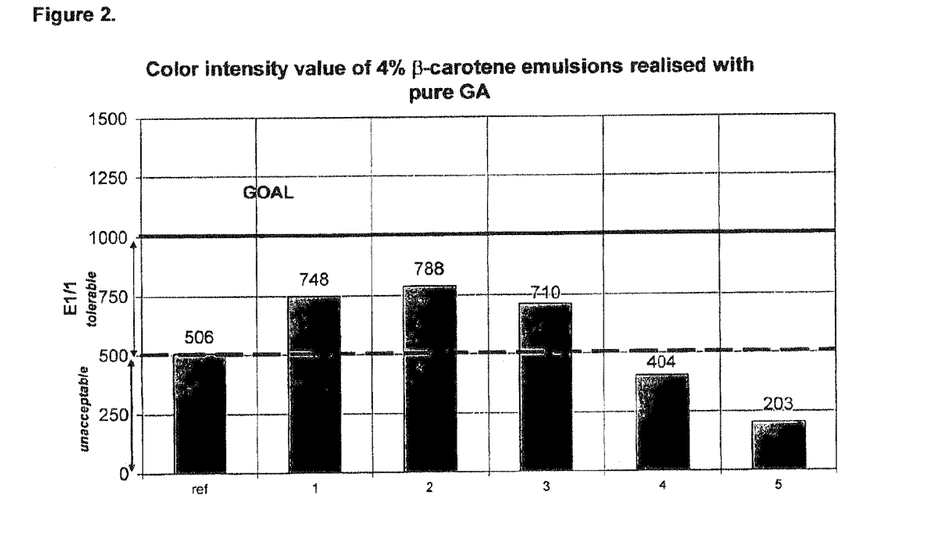
FIG. 2: Influence of the different heating time of the gum acacia on the color intensity value of emulsions containing only gum acacia. ref) not modified gum acacia; 1) gum acacia heated 1 hour/110° C.; 2) gum acacia heated 13 hours/110° C.; 3) gum acacia heated 17 hours/110° C.; 4) gum acacia heated 24 hours/110° C.; 5) gum acacia heated 38 hours/125° C.

A short heating time (below 17 hours) induces a slight increase of the emulsifying properties of the GA but longer one (higher than 24 hours), as claimed in the patent, induces the contrary. One trial realized with heated GA at higher temperature (125° C.) for longer time (38 hours) confirms its underachievement respect to the reference (see column 5).

Example 8

Effect of Heat-Treatment and Ultra-Filtration

To collect the larger molecules suspected to enhance the emulsifying properties (as disclosed in WO 2004/089991), aqueous solutions of heated GA were ultra-filtrated. This fraction was then tested on the same model system based on 4% β-carotene as in the previous examples (see FIG. 3).

Figure 3:
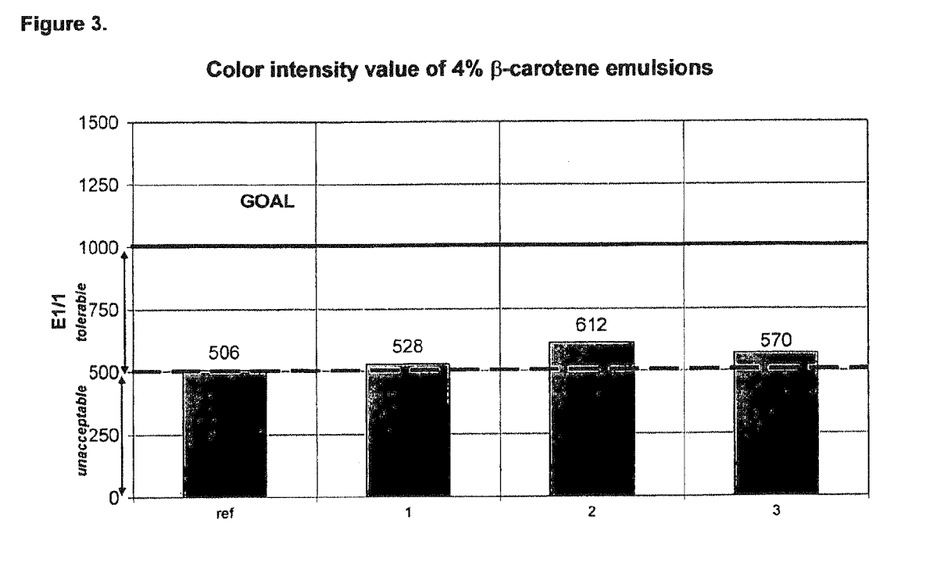
FIG. 3: Color intensity values of emulsions realized with heat-treated and ultra-filtered gum (MWCO 750 KDa). ref) not modified gum acacia; 1) gum acacia heated 1 hour/110° C.; 2) gum acacia heated 13 hours/110° C.; 3) gum acacia heated 17 hours/110° C.; 4) gum acacia heated 38 hours/110° C.

The larger molecules formed during the heat-treatment, and separated by filtration, reduced drastically emulsifying properties of the gum.

Furthermore, the E1/1 values of heated GA remain higher than the not modified one. Thus, a limited heat-treatment entailing enhancement of molecular weight and a possible protein conformation change of the GA might be one of the key factors to get higher emulsifying performances.

Example 9

Effects of Heat-Treatment of Gum Acacia Combined with the Blend Hi-Cap 100, and Maltodextrin In this example emulsions with matrix containing heat-treated gum acacia (higher molecular weight) in a blend with Hi-cap 100 (smaller molecular weight) and MD. An significant increase of the E1/1 value was observed when the emulsion is realized with GA heated up at least 13 hours at 110° C. (see FIG. 4). According to our classification, emulsions realized with gum acacia heated 17, 24 and 38 hours reached the criterion to be classified as good products when combined with the blend Hi-cap 100, and maltodextrin.

Figure 4:
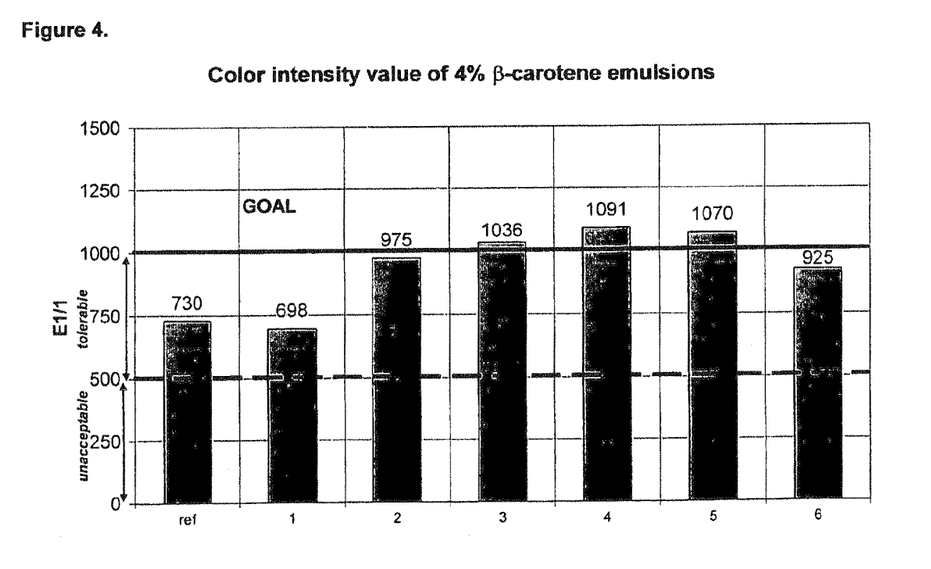
FIG. 4: Colour intensity values of emulsions realised with a blend of heat-treated gum at different time, Hi-cap 100 and MD according to a ratio 70.6%/14.6%/14.7%, and ET:10 min; ref) not modified gum; 1) GA heated 1 hour/110° C.; 2) gum acacia heated 13 hours/110° C.; 3) gum acacia heated 17 hours/110° C.; 4) gum acacia heated 24 hours/110° C.; 5) gum acacia heated 38 hours/110° C.; 6) gum acacia heated 72 hours/110° C.

These results point out 3 main observations:
1) A too short heating time (1 hour-110° C.) does not induce any change in the properties of the gum acacia
2) A too long one (72 hours) impairs slightly the improvement added to the gum by the heating process
3) Heating the gum acacia longer than 17 hours (but less than 72 hours) does not improve further its emulsifying properties.

Figure 5:
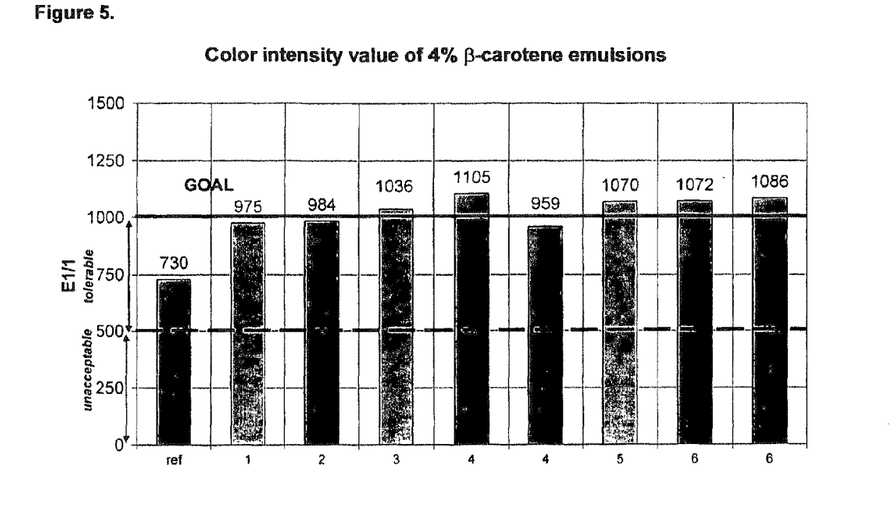
FIG. 5: Colour intensity values of emulsions realised with a blend of heat-treated, ultra-filtered (MWCO 750 KDa) GA or not, Hi-cap 100 and MD according to a ratio 70.6%/14.6%/14.7%, ET:10 min ref) not modified gum acacia; 1) GA heated 13 hours/110° C.; 2) gum acacia heated 13 hours/110° C., UF; 3) gum acacia heated 17 hours/110° C., 4) gum acacia heated 17 hours/110° C., UF; 5) gum acacia heated 38 hours/110° C.; 6) gum acacia heated 38 hours/110° C., UF.

FIG. 5 presents E1/1 value of emulsions realized with the largest molecules obtained after ultra-filtration (MWCO 750 kDa) of GA heated during 13, 17, 38 hours in a blend with Hi-cap 100 and maltodextrin. These modified GA performed as good as the non filtrated one, and better than the non modified GA. It seems that food modified starch and MD, additionally to interact with the gum for better emulsifying properties, are able to fill up the lack of smaller molecules created by Ultrafiltration.

These results indicated that increasing emulsifying properties of the gum acacia goes first of all through an internal cross-linking under specific conditions (110° C. for preferably more than 15 and less than 24 hours, preferably about 17 hours.

Example 10

Influence of the Heating Conditions

Figure 7:
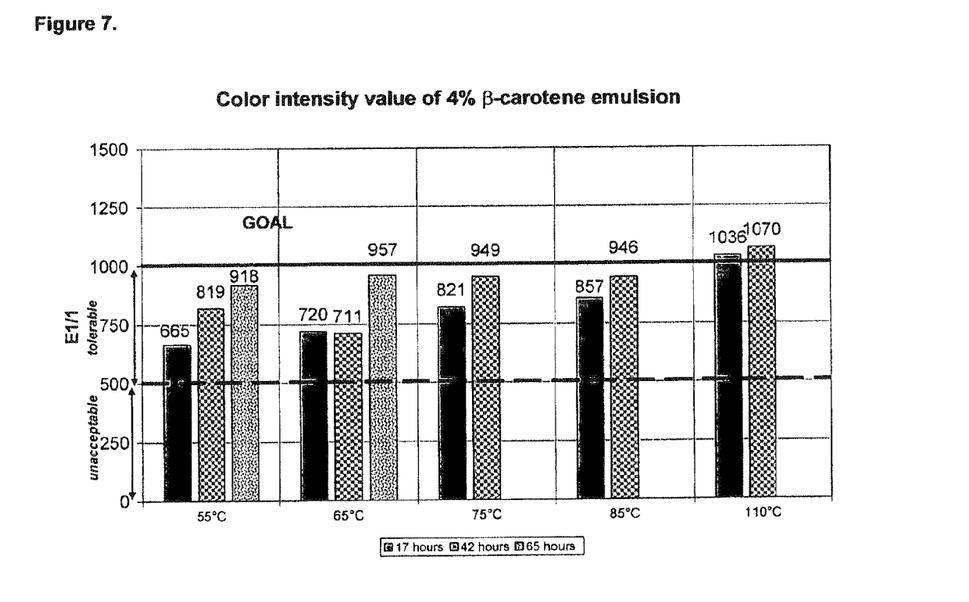
FIG. 7: Relation between E1/1 values and heating condition of GA. Modifications were performed prior to use in its solid state.

Gum acacia was then heat-treated in solid-state or in aqueous solution on softer conditions at lower temperature (55, 65, 75, 85° C.) during 17, 42, and 65 hours. Results are presented in FIGS. 7 and 8.

Realized in liquid state and softer conditions, the treatment seems to be sufficient to get an internal modification of the GA structure (FIG. 6) because E1/1 values are higher than 500 but not as good as modifications carried out through harder conditions.

Figure 6:
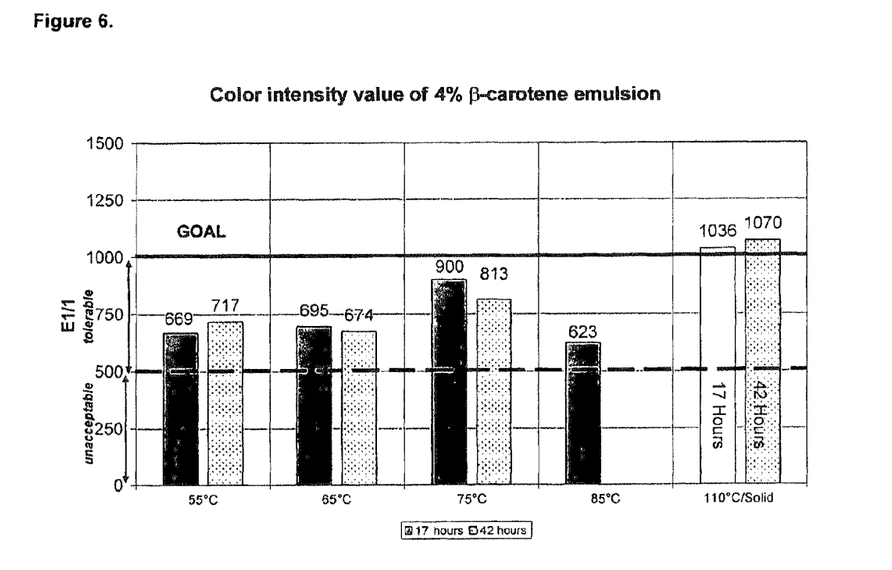
FIG. 6: Relation between E1/1 values and heating condition of GA. Modifications were performed prior to use in a liquid state. Concentration of GA was about 37.5% in weight.

At temperatures below 65° C., we observed no significant difference between samples heated 17 or 42 hours;
GA treated at 75° C. had the highest E1/1 value, but lower than GA modified in solid state at 110° C. for 17 hours;
85° C. seems to be overheated for the liquid state (decrease of E1/1 value).

Out of these observations, it results that heat-treatment on liquid state is possible, but compared to solid state (110° C.) gums performed differently and not as well.

Results obtained with GA heated on softer conditions in solid state (FIG. 7) indicated a slight increase of the E1/1 value as one goes along an increase of the time for one selected temperature. But, these increases were not high enough to reach the value of the GA heat treated at 110° C. during about 17 hours.

Figure 8:
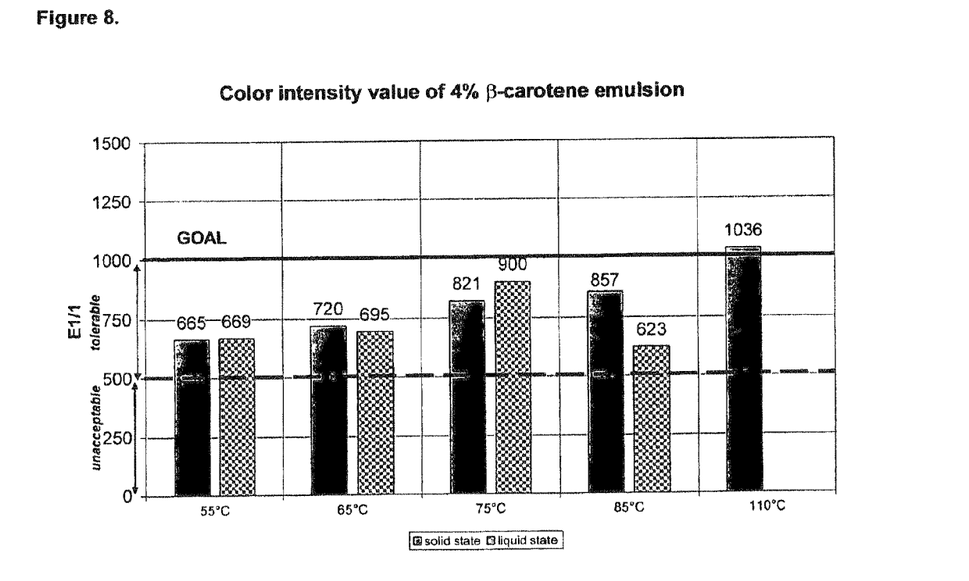
FIG. 8: Relation between E1/1 values of GA cross linked 17 hours at different temperatures and different states. Concentration of GA in aqueous solution was about 37.5% in weight.

Any change induced by the thermal treatment of the gum acacia (in liquid or solid state in softer conditions) is visible in the emulsifying properties of the gum (increase of E1/1 value) (FIG. 8). In spite of these observations, the generated GA confered the best properties to the carotenoid compositions, when heated at 110° C. for preferably more than 15 and less than 24 hours, more preferably for about 17 hours. Thereby, there is a strong relationship between time and temperature for the modification of the GA.

The invention claimed is:

1. A composition for the enrichment, fortification and/or coloration of a food, beverage, animal feed, cosmetic, or pharmaceutical, said composition comprising effective amounts of a modified gum acacia and at least one carotenoid, wherein the modified gum acacia has been subjected to a heat-treatment at a temperature between 100° C. and 115° C. for 13 to 38 hours, characterized in that the composition comprises less than 40 weight-% oil, based on the total composition in dry matter, wherein the composition further comprises octenyl succinic anhydride modified food starch and one or more adjuvants and/or excipients, wherein said one or more adjuvants and or/excipients comprises maltodextrin, and wherein (the amount of modified gum acacia)/(the amounts of modified gum acacia+the amount of octenyl succinic anhydride modified food starch+the amount of maltodextrin)>=70%.

2. The composition according to claim 1, wherein the composition comprises between 0.1-50 weight-% carotenoids, based on the total composition in dry matter.

3. The composition according to claim 1, wherein the at least one carotenoid is β-carotene.

4. The composition according to claim 1, wherein the heat-treatment of gum acacia is performed for more than 15 and less than 24 hours.

5. The composition according to claim 1, wherein the gum acacia is acacia senegal.

6. The composition according to claim 1, wherein the composition possesses a color intensity value (E1/1) of at least 500, wherein the color intensity E1/1 is the absorbance of a 1% solution and a thickness of 1 cm and is calculated as follows: E1/1=(Amax-A650)*dilution factor/(weight of sample*content of product form in %).

7. A process for the manufacture of the composition according to claim 1 comprising:
I) dissolving gum acacia, which has been modified by a heat-treatment at a temperature between 100 C and 115 C for 14 to 38 hours, in water, to form a solution,
II) adding an organic solvent to a mixture of at least one carotenoid, octenyl succinic anhydride modified food starch, and maltodextrin, and
III) combining the mixture of step H with the solution of step I),
characterized in that the composition comprises less than 40 weight-% oil, based on the total composition in dry matter.

8. The process according to claim 7, further comprising the steps of:
IV) emulsifying the combination of step ill, and
V) drying the emulsion.

9. The process according to claim 8, wherein polysaccharides are also added in step II).

10. A method for the enrichment, fortification and/or coloration of food, beverages, animal feed, cosmetics or pharmaceutical compositions comprising adding the composition of claim 1 thereto.

11. A process for the manufacture of a beverage comprising mixing an effective amount of the composition according to claim 1 with a beverage.

* * * * *